(12) United States Patent
Inoue et al.

(10) Patent No.: US 10,898,226 B2
(45) Date of Patent: Jan. 26, 2021

(54) OOCYTE COLLECTION NEEDLE

(71) Applicants: KITAZATO CORPORATION, Tokyo (JP); NATURAL ART RESEARCH INSTITUTE, LTD., Tokyo (JP)

(72) Inventors: Futoshi Inoue, Tokyo (JP); Shokichi Teramoto, Tokyo (JP)

(73) Assignees: KITAZATO CORPORATION, Shizuoka (JP); NATURAL ART RESEARCH INSTITUTE, LTD., Tokyo (JP)

(*) Notice: Subject to any disclaimer, the term of this patent is extended or adjusted under 35 U.S.C. 154(b) by 173 days.

(21) Appl. No.: 15/746,944

(22) PCT Filed: Jul. 21, 2016

(86) PCT No.: PCT/JP2016/071462
§ 371 (c)(1),
(2) Date: Jan. 23, 2018

(87) PCT Pub. No.: WO2017/014289
PCT Pub. Date: Jan. 26, 2017

(65) Prior Publication Data
US 2018/0214179 A1    Aug. 2, 2018

(30) Foreign Application Priority Data
Jul. 23, 2015 (JP) .................. 2015-146241

(51) Int. Cl.
*A61B 17/435* (2006.01)
*A61B 17/42* (2006.01)
(Continued)

(52) U.S. Cl.
CPC .......... *A61B 17/435* (2013.01); *A61B 10/02* (2013.01); *A61B 17/42* (2013.01); *A61B 17/43* (2013.01)

(58) Field of Classification Search
CPC .......... A61B 17/425–435; A61B 10/02; A61B 10/0233; A61B 10/0283; A61B 10/0291;
(Continued)

(56) References Cited

U.S. PATENT DOCUMENTS

| 2002/0095066 A1* | 7/2002 | Kamrava | ............... A61B 1/303 |
| | | | 600/34 |
| 2010/0036193 A1 | 2/2010 | Pizolato | |

(Continued)

FOREIGN PATENT DOCUMENTS

| CN | 101715322 | 5/2010 |
| CN | 103735288 | 4/2014 |

(Continued)

OTHER PUBLICATIONS

Extended European Search Report dated May 16, 2019 in European Patent Application No. 16827849.7.
(Continued)

*Primary Examiner* — Catherine B Kuhlman
(74) *Attorney, Agent, or Firm* — Wenderoth, Lind & Ponack, L.L.P.

(57) ABSTRACT

A needle employs a three-stair-stepped structure including a front-end small diameter part, an intermediate part, and a large diameter part. The front-end small diameter part and the intermediate part are in fluid communication with each other by a first tapered part, and the intermediate part and the large diameter part are in fluid communication with each other by a second tapered part. The internal diameter of the front-end small diameter part is made so as to be equal to or greater than 0.35 mm based on the allowable deformation level of a cumulus oocyte complex, the outer diameter is made so as to be equal to or smaller than 0.7 mm based on the size of a small follicle, and the inclination angle of the
(Continued)

inclined acicular end, and the length is made so as to be 10-25 mm based on the size of a dominant follicle.

6 Claims, 5 Drawing Sheets

(51) Int. Cl.
*A61B 10/02* (2006.01)
*A61B 17/43* (2006.01)

(58) Field of Classification Search
CPC ....... A61B 2010/045; A61D 19/02–04; A61M 5/3286; A61M 5/329
See application file for complete search history.

(56) References Cited

U.S. PATENT DOCUMENTS

2010/0179377 A1* 7/2010 Hagby ............... A61B 10/0283 600/33
2015/0327887 A1 11/2015 Inoue

FOREIGN PATENT DOCUMENTS

| | | | | |
|---|---|---|---|---|
| JP | 62-64344 | 3/1987 | | |
| JP | 2001-252293 | 9/2001 | | |
| JP | 2001252293 A * | 9/2001 | | |
| JP | 2004-329745 | 11/2004 | | |
| JP | 3149897 | 4/2009 | | |
| JP | 2013-141488 | 7/2013 | | |
| WO | 2010/054660 | 5/2010 | | |
| WO | WO-2010054660 A1 * | 5/2010 | ......... | A61B 10/0283 |
| WO | WO-2014115304 A1 * | 7/2014 | ......... | A61B 10/0233 |

OTHER PUBLICATIONS

International Search Report dated Sep. 27, 2016 in International Application No. PCT/JP2016/071462.

Chinese Search Report dated Dec. 3, 2019 in Chinese Patent Application No. 201680043153.1, with English Translation.

* cited by examiner

OOCYTE COLLECTION NEEDLE

TECHNICAL FIELD

The present disclosure relates to an oocyte collection needle for percutaneously collecting an oocyte.

BACKGROUND ART

In-vitro fertilization typically employs a scheme of injecting hormonal agents to stimulate follicular development so that oocytes from multiple developed follicles can be collected. With this scheme, multiple follicles of relatively uniform size of substantially 20 mm in diameter can be obtained, enabling the collection of a mature oocyte from each follicle.

However, as the follicle develops and increases in size, the amount of bleeding caused by penetrating a tissue may be increased, creating the risk of intraperitoneal bleeding. In addition, depending on the amount of hormonal agent administered, several problems, including the delayed recovery of ovarian function and a decreased response to the administered hormone, may arise.

Hence, in recent years, an oocyte collection scheme based on the natural cycle, which eliminates such problems, has been attracting attention. This scheme uses no hormonal agent, and instead a mature oocyte is collected from a dominant follicle (developed follicle) developed in the natural cycle. However, under this scheme, only one oocyte is obtainable per collection.

In the meantime, with the oocyte collection scheme based on the natural cycle, if oocytes can be collected from so-called small follicles (rudimentary follicles other than the dominant follicle) for the purpose of in-vitro maturation, the number of collectable oocytes per collection increases, making the oocyte collection in the natural cycle more efficient.

However, since conventional oocyte collection needles are not designed for collecting oocytes from the small follicles, they cannot be easily used for collecting oocytes from follicles other than the dominant follicle.

For example, Patent Document 1 discloses a sampling needle for oocyte retrieval from a human subject. The front end (first tubular region) of this sampling needle has an internal diameter that is equal to or greater than 0.2 mm since the size of the oocyte is 0.1-0.2 mm. When an oocyte is retrieved, however, it is aspirated as a cumulus oocyte complex which is made up of an oocyte and the cumulus cells that surround the oocyte. Therefore, if the internal diameter of the needle is too small, the oocyte may be distorted at the time of aspiration, or the aspiration speed may be decreased. Hence, in practice, unless the internal diameter is increased to some extent, the application of this sampling needle for oocyte collection from a dominant follicle is difficult. At the same time, if the internal diameter is increased, the external diameter increases in turn, making a precise insertion of the needle tip to a small follicle difficult. In addition, if separate needles are used for collecting oocytes from the dominant follicle and from small follicles, the efficiency of the oocyte collection procedure is undermined.

CITATION LIST

Patent Literatures

Patent Document 1: Japan Patent No. 5342554

SUMMARY OF INVENTION

Technical Problem

The present disclosure has been made in view of such foregoing circumstances, and the objective is to provide an oocyte collection needle capable of collecting an oocyte not only from the dominant follicle (developed follicle) but also from small follicles (rudimentary follicles) through sequential collection procedure with as little negative impact as possible on the human body.

Solution to Problem

The inventors of the present disclosure found that the size of a small follicle which contains an oocyte suitable for in-vitro maturation is equal to or greater than substantially 5 mm. In addition, the size of a cumulus oocyte complex which contains an oocyte that has a diameter of substantially 0.1 mm is 0.3-0.5 mm in the case of a dominant follicle, and smaller in the case of a small follicle. Hence, in view of the allowable deformation level of the cumulus oocyte complex end the aspiration speed, it is preferable that the internal diameter of the needle front end (a "front-end small diameter part" to be explained later) should be equal to or greater than 0.35 mm, and, even more, that it be equal to or greater than 0.4 mm. In addition, it is appropriate that the outer diameter of the needle front end should be equal to or smaller than 0.7 mm, and the front end of such a needle front end should be formed by an inclined acicular end of substantially 10-20 degrees. This enables the inclined end surface to have a length equal to or shorter than 4 mm while maintaining the inclined acicular end at an angle practical for inserting into the small follicle to aspirate the cumulus oocyte complex.

Conversely, it is preferable that the length of the needle front end should be equal to or greater than the diameter of the dominant follicle. This enables only the needle front end to be inserted into the follicle for both the dominant and small follicles. In addition, it is preferable that the internal diameter of the next stair-stepped part (an "intermediate part" to be explained later) continuous from the needle front end should be greater than the internal diameter of the needle front end in order to let the cumulus oocyte complex recover from the deformation and to eliminate speedily any adverse effects on the oocyte. Since the cumulus oocyte complex is to be aspirated with a follicular fluid, if the internal diameter of the next stair-stepped part is too large, the flow of follicular fluid may be disturbed around the entry to the next stair-stepped part and may have an adverse effect on the oocyte. Hence, in view of the normal aspiration pressure (for example, substantially 100-300 mHg), it is necessary to set the internal diameter so as to have a change rate causing little or no disturbance. In addition, it is preferable that the outer diameter should be small so as not to have an adverse effect on the collection procedure such as puncturing tissue.

More specifically, the oocyte collection needle according to the present disclosure includes:
 a front-end small diameter part provided with a front end to be inserted in a human body;
 an intermediate part in communication with the front-end small diameter part via a first tapered part fluidly in communication with the front-end small diameter part, the intermediate part having a larger internal diameter and outer diameter than the internal diameter of the front-end small diameter, part and the outer diameter thereof; and a large diameter part in communication with the intermediate part via a second tapered part fluidly in communication with the intermediate part, the large diameter part having a larger internal diameter and outer diameter than the internal diameter of the intermediate part and the outer diameter thereof, in which:

the internal diameter of the front-end small diameter part is made so as to be equal to or greater than 0.35 mm, or, more preferably, equal to or greater than 0.4 mm, the outer diameter is made so as to be equal to or smaller than 0.7 mm, or, more preferably, equal to or smaller than 0.6 mm, the length is made so as to be substantially 10-40 mm, or, more preferably, equal to or greater than 20 mm and less than 30 mm, the front end is formed as an inclined acicular end with an inclination angle of substantially 10-20 degrees;

the internal diameter of the intermediate part is made so as to be equal to or greater than substantially 0.45 mm, or, more preferably, equal to or greater than substantially 0.5 mm, and the outer diameter is made so as to be equal to or smaller than 0.9 mm, or, more preferably, equal to or smaller than 0.8 mm;

the first tapered part is in communication with the front-end small diameter part and the intermediate part at an average gradient equal to or smaller than substantially 10% for both the outer diameter and the internal diameter, or, more preferably, equal to or smaller than 6%:

the length including the front-end small diameter part, the first tapered part, and the intermediate part is substantially 60-150 mm, or, more preferably, substantially 110-130 mm; and the octal length including the front-end small diameter part, the first tapered part, the intermediate part, the second tapered part, and the large diameter part is substantially 200-500 mm, or, more preferably, substantially 250-350 mm.

It is preferable that the internal diameter of the large diameter part should be equal to or greater than substantially 0.7 mm, and the outer diameter thereof should be equal to or greater than 1.1 mm in view of operability and stability. In addition, the size of the second tapered part in the lengthwise direction is not limited to any particular size, and is appropriate as long as the second tapered part is in communication with the intermediate part and with the large diameter part at a constant average gradient.

The large diameter part has a suitable length to pass through a vagina when the needle is used, and the portion defined by the front-end small diameter part, the first tapered part, and the intermediate part has a suitable length to contact the cumulus oocyte complex to be collected without causing the second tapered part and the large diameter part to penetrate a human tissue.

In addition, the front-end small diameter part has a suitable length to contact the cumulus oocyte complex to be collected without causing the first tapered part and the intermediate part to penetrate a follicle (dominant follicle or small follicle).

Advantageous Effects of Invention

According to the present disclosure, oocytes can be collected from both dominant and small follicles through a sequential collection procedure. Hence, multiple puncturing of a vaginal wall, or a peritoneum that will be a cause of pain is rendered unnecessary, reducing the burden or the human body.

In particular, according to the present disclosure, only the front-end small diameter part is made so as to penetrate the dominant follicle or the small follicle, and the front end is allowed to accurately contact the cumulus oocyte complex to be collected. In addition, since the oocyte aspirated via the front-end small diameter part is immediately transferred to an intermediate part, risk of causing deformation to the oocyte is kept to a minimum.

DESCRIPTION OF EMBODIMENTS

Figure 1:
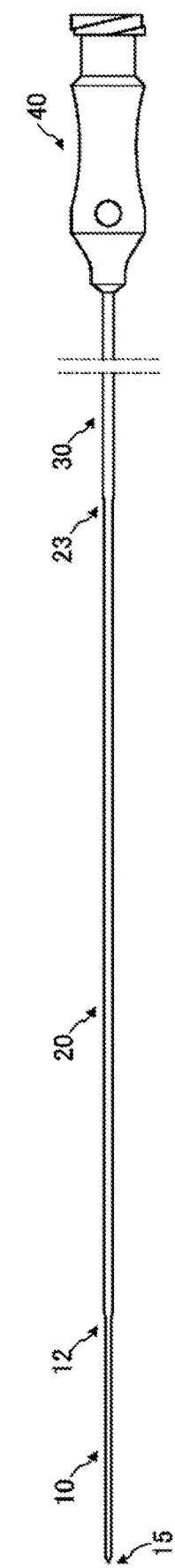
FIG. 1 is an external shape diagram illustrating an oocyte collection needle according to the embodiment of the present disclosure.
Figure 2:
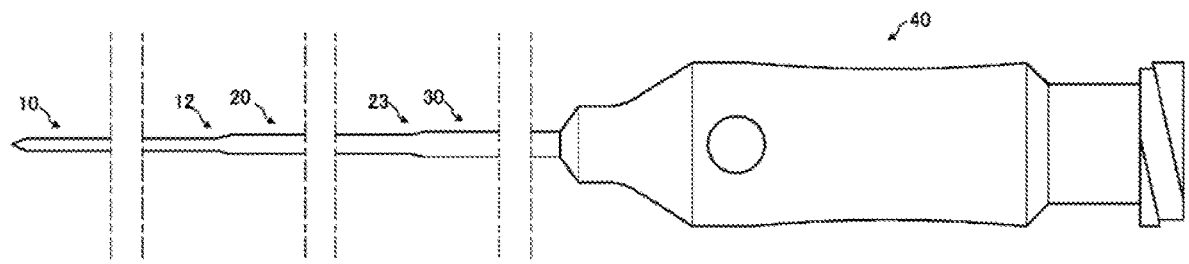
FIG. 2 is a plan view of the oocyte collection needle according to the embodiment of the present disclosure.
Figure 3:
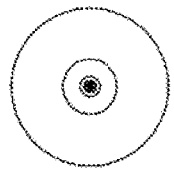
FIG. 3 is a left side-view of the oocyte collection needle according to the embodiment of the present disclosure.
Figure 4:
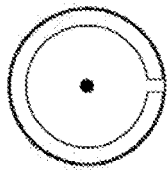
FIG. 4 is a right side-view of the oocyte collection needle according to the embodiment of the present disclosure.
Figure 5:
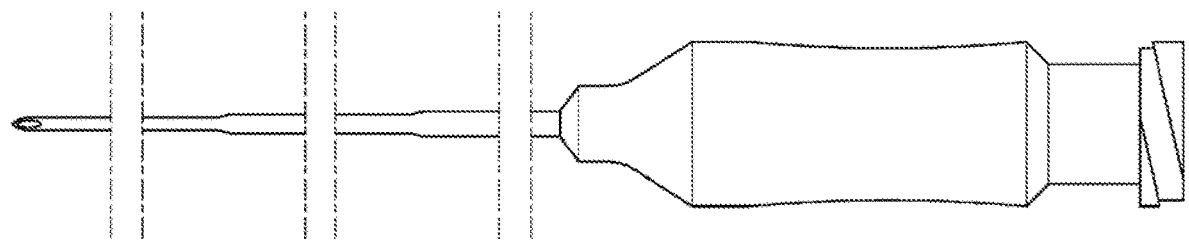
FIG. 5 is a bottom view of the oocyte collection needle according to the embodiment of the present disclosure.
Figure 6:
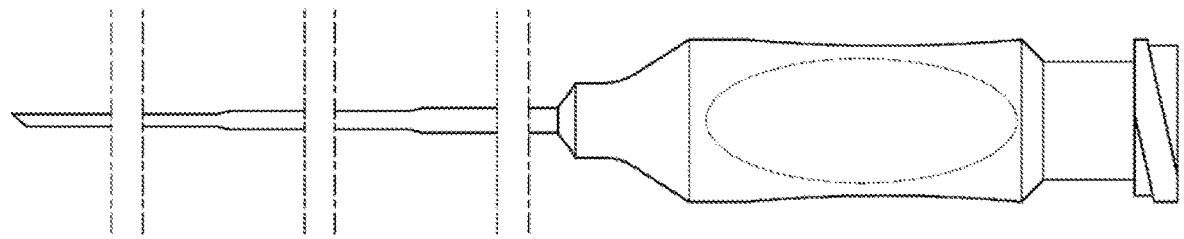
FIG. 6 is a front view of the oocyte collection needle according to the embodiment of the present disclosure.
Figure 7:
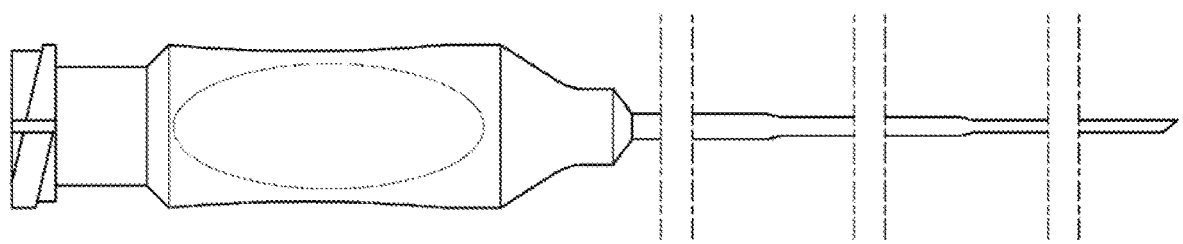
FIG. 7 is a back view of the oocyte collection needle according to the embodiment of the present disclosure.

An oocyte collection needle according to an embodiment of the present disclosure will be explained with reference to the figures. FIG. 1 is an external shape diagram of an oocyte collection needle 1 according to this embodiment, and FIGS. 2-7 are each a six-sided view represented by an orthographic drawing scheme. A single dashed chain line in the figures indicates the omission of a continuous part since the same shape continues.

This oocyte collection needle includes, from the front end of the needle, three regions: a front-end small diameter part 10, an intermediate part 20 and a large diameter part 30, which have different thicknesses. Provided between the front-end small diameter part 10 and the intermediate part 20 is a first tapered part 12 that successively changes the diameter size, and likewise a second tapered part 23 is provided between the intermediate part 20 and the large diameter part 30. A finger grip 40 to manipulate the oocyte collection needle 1 is provided at the basal end of the large diameter part 30.

The respective regions will be explained below in detail.

Front-End Small Diameter Part

It is appropriate that the internal diameter or the front-end small diameter, part 10 should be determined in view of the size of not an oocyte but the cells or tissue aspirated together with the oocyte. The diameter of an oocyte is substantially 0.1 mm, and a membrane called the zona pellucida is present around the oocyte, and thus the maximum diameter is substantially 0.15 mm. In addition, a cumulus oocyte complex containing cumulus cells surrounding such a membrane has a size which is two to three times as much as the foregoing maximum diameter, and which is substantially 0.3-0.45 mm. Still further, when the allowable deformation level of the cumulus oocyte complex is substantially 10%, in view of the slight variability in size of the cumulus oocyte complex, it is necessary that the internal diameter of the front-end small diameter part 10 should be equal to or greater than substantially 0.35 mm, and preferably, equal to or greater than substantially 0.4 mm.

In the meantime, when the internal diameter becomes narrower, the aspiration time increases. Hence, the aspiration pressure is increased, but the adverse effect on an oocyte due to the deformation of the cumulus oocyte complex increases correspondingly to the increase in aspiration pressure. When, for example, an oocyte is aspirated at 200 mmHg via a conventional two-stair-stepped structure oocyte collection needle (a straight needle that has a total length of 300 mm including a front-end small diameter part which has an internal diameter of 0.4 mm and a length of 100 mm), it takes substantially 20 seconds to aspirate 1 cc (1 ml). In view of the effect on an oocyte, however, it is necessary to reduce such a time to be equal to or shorter than substantially 10 seconds. By applying the oocyte collection needle according to this embodiment, such an objective is accomplished, as will be explained later.

Figure 8:
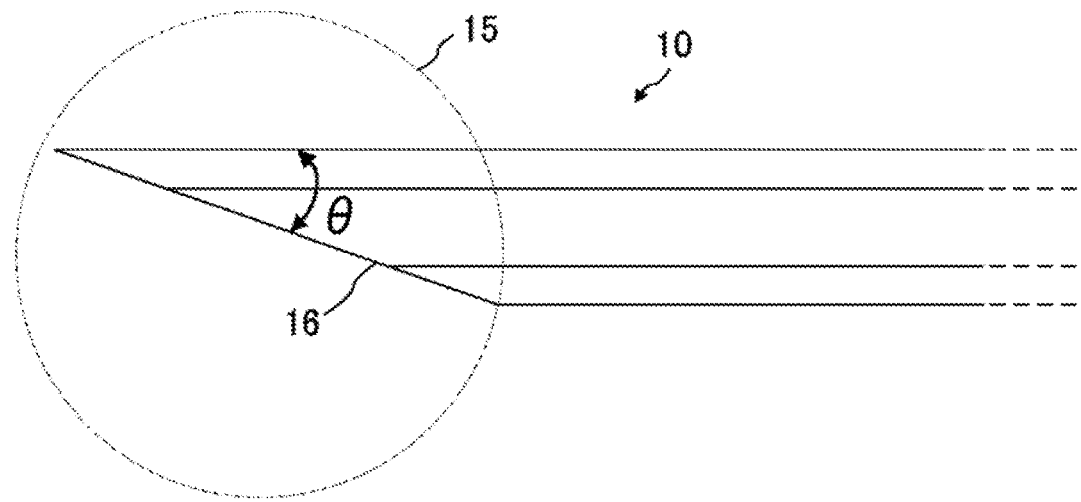
FIG. 8 is an explanatory diagram for the inclination angle $\theta$ of an inclined acicular end as in FIG. 1.

The inclined acicular end 15 has an inclination angle that is substantially 15 degrees in most cases, and in practice, an inclination angle within the range between 10 to 20 degrees is used. In order to collect an oocyte that can be matured by in-vitro maturation from a small follicle that is of a size of substantially 5 mm, it is preferable that the outer diameter of the inclined acicular end 15 should be equal to or smaller than 0.7 mm. Hence, as illustrated in FIG. 8, the end surface (inclined end surface) 16 of the inclined acicular end 15 becomes substantially 4 mm in size at a maximum, and the inclined acicular end 15 is completely held within the small follicle, enabling aspiration of the cumulus oocyte complex and follicular fluid. In order to facilitate puncturing of the small follicle by the acicular end, it is preferable that the inclination angle θ should be equal to or smaller than 15 degrees. When the outer diameter of the inclined acicular end 15 is set to be equal to or smaller than 0.6 mm, oocyte collection from a small follicle as small as substantially 3 mm is enabled.

In addition, in view of the size of the dominant follicle, it is preferable that the length of the front-end small diameter part 10 should be equal to or longer than such a size. This allows only the front-end small diameter part 10 to be inserted into both the dominant follicle and the small follicle, and no other regions of the needle are inserted therein. This facilitates the puncturing procedure.

Since the size (diameter) of the dominant follicle is substantially 20 mm at a maximum, in view of the variability and of the margin, it is preferable that the length of the front-end small diameter part 10 should be substantially 10-25 mm, or, more preferably, substantially 15-20 mm.

Intermediate Part

In order speedily to eliminate any adverse effects caused by the front-end small diameter part 10 on the cumulus oocyte complex, and eventually on the oocyte, it is preferable that the internal diameter of the intermediate part 20 should be of a size that is substantially the size of the cumulus oocyte complex. Hence, it is preferable that the internal diameter of the intermediate part 20 should be made so as to be equal to or greater than substantially 0.45 mm, or, more preferably, equal to or greater than substantially 0.5 mm. The outer diameter of the intermediate part 20 is determined based on the internal diameter, but in view of the operability at the time of puncturing, it is preferable that the difference relative to the outer diameter of the front-end small diameter part 10 should be as small as possible. In practice, there is no technical problem when such a difference relative to the outer diameter of the front-end small diameter part 10 is equal to or smaller than substantially 0.2 mm.

First Tapered Part

The inventors of the present disclosure found that, when a difference in the internal diameter between the front-end small diameter part 10 and the intermediate part 20 is too large, a convection flow is likely to be caused within the needle tube at the time of aspiration, and a degeneration of the oocyte is likely to occur due to the convection flow and bubbles originating from the flow. This may be caused by the abrupt recovery of the cumulus oocyte complex from the deformed condition and a disturbance in the flow of the follicular fluid originating from the occurrence of eddying flow. In addition, in the aspiration procedure, since the follicle itself is eventually suctioned, a drastic change in flow may affect the oocyte by causing damage to the zona pellucida, destroying the oocyte itself in some cases.

It is preferable, in order not to cause adverse effects on the aspiration time, that the internal diameter of the first tapered part 12 should be formed at an average gradient that is equal to or smaller than substantially 10%, or, more preferably, substantially 6%.

The front-end small diameter part 10, the first tapered part 12, and the intermediate part 20 have been explained above, and it is preferable that the total length of those parts should be a length that does not allow the second tapered part 23 and the large diameter part 30, to be explained later, to penetrate any tissues of the human body. More specifically, it is preferable that such a length should be substantially 60-150 mm, or, more preferably, in view of the margin to some extent and the operability at the time of puncture, substantially 100-130 mm.

Large Diameter Part, Second Tapered Part

It is appropriate if the large diameter part 30 has a larger internal diameter and outer diameter than those of the intermediate part 20, and has a suitable length to properly enable the oocyte collection needle 1 to pass through a vagina. In addition, the second tapered part 23 does not have a limitation on its average gradient as long as it can cause the intermediate part 20 to be in fluid communication with the large diameter part 30.

Next, with reference to FIGS. 9 and 10, the function of the oocyte collection needle 1 according to this embodiment will be explained.

Figure 9:
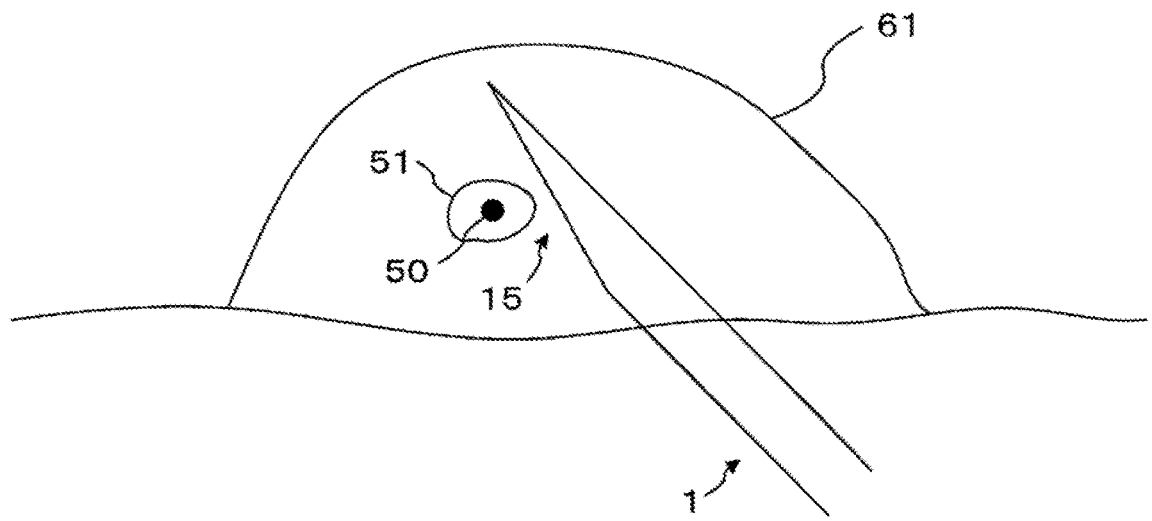
FIG. 9 is an explanatory diagram illustrating the puncturing condition of a small follicle according to the embodiment of the present disclosure.
Figure 10:
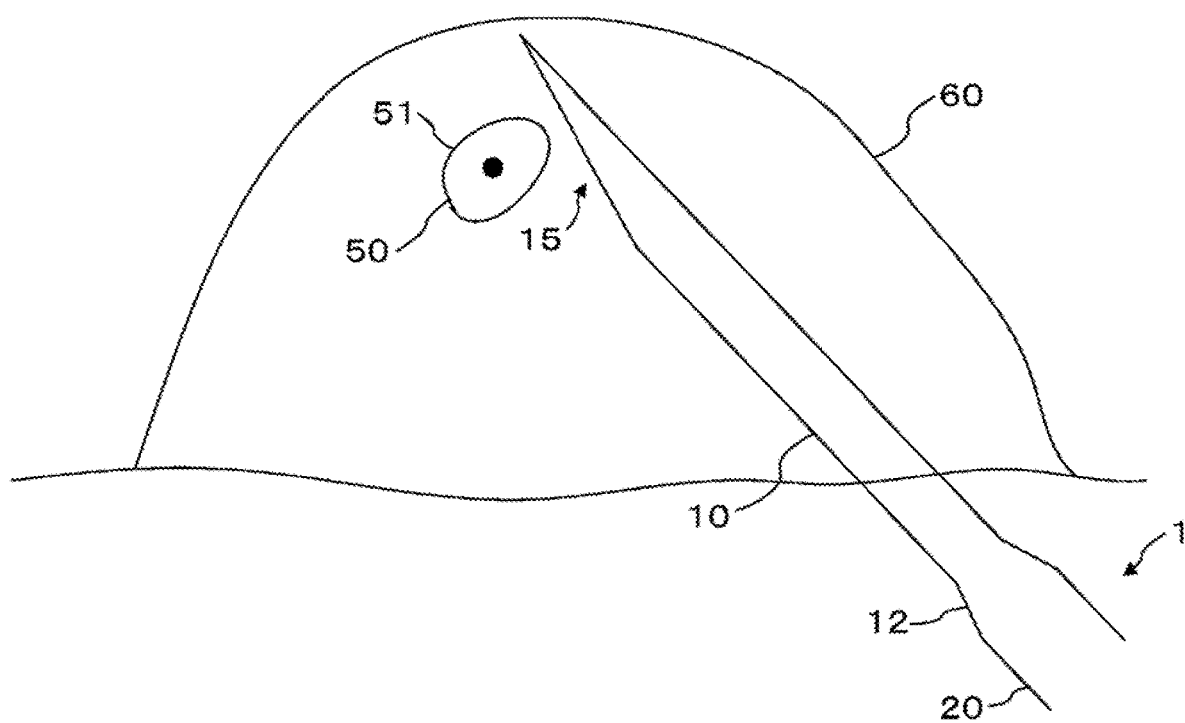
FIG. 10 is an explanatory diagram illustrating the puncturing condition of a dominant follicle according to the embodiment of the present disclosure.

When the above oocyte collection needle 1 is caused to penetrate a small follicle 61, as illustrated in FIG. 9, the inclined acicular end 15 of the front-end small diameter part 10 is completely held within the small follicle 61. This enables aspiration of the cumulus oocyte complex 51 that contains the oocyte 50 within the small follicle 61. In addition, when the oocyte collection needle 1 is caused to penetrate the dominant follicle 60, as illustrated in FIG. 10, only the front-end small diameter part 10 is held within the dominant follicle 60. That is, since the front-end small diameter part 10 has substantially the same length as or a greater length than the diameter of the dominant follicle, in the aspiration procedure of the cumulus oocyte complex 51 within the dominant follicle 60, the intermediate part 20 and the first tapered part 12 that have a larger outer diameter than that of the front-end small diameter part 10 are not inserted in the dominant follicle 60, and such an insertion is not necessary at all. Hence, the collection procedure can be carried out efficiently without disrupting the operability of the oocyte collection needle 1.

Figure 11:
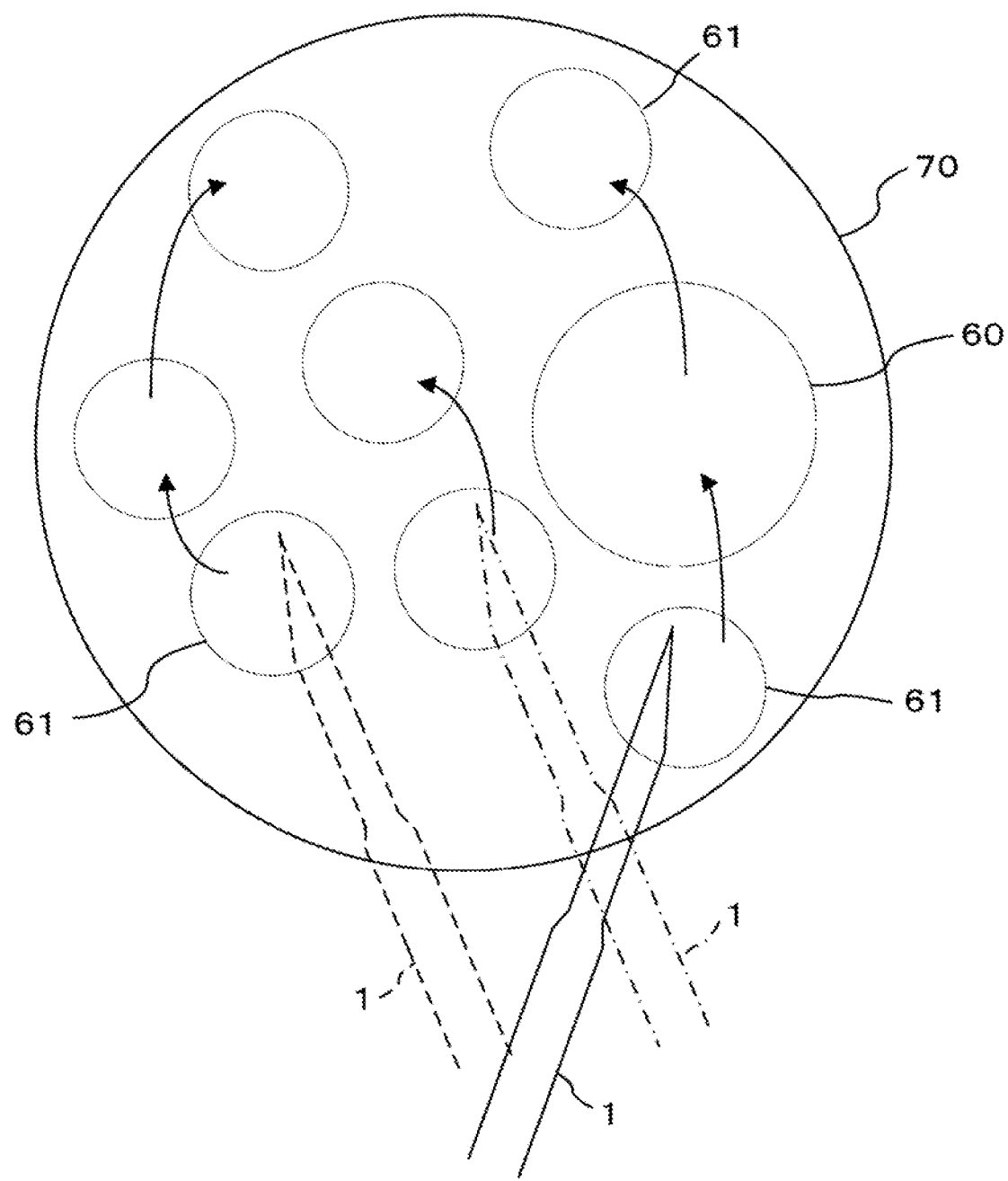
FIG. 11 is an explanatory diagram illustrating an oocyte collection procedure according to the embodiment of the present disclosure.

As for the sequential oocyte collection procedure, as illustrated in FIG. 11, cumulus oocyte complexes in follicles are collected with the oocyte collection needle 1 inserted within an ovary 70 in a unicursal-sequence manner as much as possible. On this occasion, as in the collection route of the oocyte collection needle 1 indicated by the continuous line in FIG. 11, the oocyte collection needle 1 can be inserted into the follicle regardless of whether such a follicle is the small follicle 61 or the dominant follicle 60. In addition, when just the collection route needs to be changed, as in the oocyte collection needle 1 indicated by a dashed chain line in FIG. 11, the collection route can be changed while simply changing the direction of the inclined acicular end 15 without re-puncturing the ovary 70 with the oocyte collection needle 1. As for follicles that are not collectable by a single puncturing procedure to the ovary 70, as in the oocyte collection needle 1 indicated by a dashed line in FIG. 11, puncturing is performed at a new suitable location, and the oocyte is collected. In this case, also, a new puncturing procedure to a vaginal wall or a peritoneum (unillustrated) that will be a cause of pain is not required, and the large diameter part 30 is not inserted in such human tissues.

First Example

In this example, an oocyte collection test was carried out using an oocyte collection needle 1 that had a front-end small diameter part 10 which was 22 Gauge (outer diameter: 0.70 mm, and internal diameter: 0.48 mm) and which had a length of 20 mm, an intermediate part 20 which was 21 Gauge (outer diameter: 0.80 mm, and internal diameter: 0.57 mm), a large diameter part 30 which was 18 Gauge (outer diameter: 1.20 mm, and internal diameter: 0.94 mm), a first tapered part 12 which had a length of 5 mm and which had an average gradient for the internal diameter that was 6%, and a second tapered part 23 which had a length of 5 mm and which had an average gradient of 6%. The length from the tip of the front-end small diameter part 10 to the basal end of the intermediate part 20 was 110 mm, and the length from the tip of the front-end small diameter part 10 to the basal end of the large diameter part 30 was 300 mm. The test facilities are disclosed in, for example, Patent Document 1, FIG. 2, and thus the explanation thereof will be omitted (the same is true in the following explanation).

The necessary times for aspirating 1 ml at an aspiration pressure of 100 mmHg were 0.5 seconds, 9.3 seconds, and 9.0 seconds. In addition, the necessary times for aspirating 1 ml at the aspiration pressure of 200 mmHg were 5.6 seconds, 5.4 seconds, and 5.5 seconds.

Second Example

In this example, an oocyte collection test was carried out using an oocyte collection needle 1 that had a front-end small diameter part 10 which was 23 Gauge (outer diameter: 0.65 mm, and internal diameter: 0.40 mm) and which had a length of 20 mm, an intermediate part 20 which was 22 Gauge (outer diameter: 0.70 mm, and internal diameter: 0.48 mm), a large diameter part 30 which was 18 Gauge (outer diameter: 1.20 mm, and internal diameter: 0.94 mm), a first tapered part 12 which had a length of 5 mm and which had an average gradient for the internal diameter that was 6%, and a second tapered part 23 which had a length of 5 mm and which had an average gradient of 6%. The length from the tip of the front-end small diameter part 10 to the basal end of the intermediate part 20 was 110 mm, and a length from the tip of the front-end small diameter part 10 to the basal end of the large diameter part 30 was 300 mm.

The necessary times for aspirating 1 ml at an aspiration pressure of 100 mmHg were 17.1 seconds, 18.8 seconds, and 19.2 seconds. In addition, the necessary times for aspirating 1 ml at an aspiration pressure of 200 mmHg were 10.2 seconds, 11.4 seconds, and 12.0 seconds.

Third Example

In this example, an oocyte collection test was carried out using an oocyte collection needle 1 that had a front-end small diameter part 10 which was 23 Gauge (outer diameter: 0.65 mm, and internal diameter: 0.40 mm) and which had a length of 20 mm, an intermediate part 20 which was 21 Gauge (outer diameter: 0.80 mm, and internal diameter: 0.57 mm), a large diameter part 30 which was 18 Gauge (outer diameter: 1.20 mm, and internal diameter: 0.94 mm), the first tapered part 12 which had a length of 5 mm and which had an average gradient of the internal diameter that was 6%, and a second tapered part 23 which had a length of 5 mm and which had an average gradient of 6%. The length from the tip of the front-end small diameter part 10 to the basal end of the intermediate part 20 was 110 mm, and the length from the tip of the front-end small diameter part 10 to the basal end of the large diameter part 30 was 300 mm.

The necessary times for aspirating 1 ml at an aspiration pressure of 100 mmHg were 12.1 seconds, 11.9 seconds, and 11.4 seconds. In addition, the necessary times for aspirating 1 ml at an aspiration pressure of 200 mmHg were 7.3 seconds, 7.1 seconds, and 7.4 seconds.

Fourth Example

Comparison Test by Two Stair-Stepped Structure

In this example, a comparison test was carried out using an oocyte collection needle 1 that had no intermediate part 20, but had a front-end small diameter part 10 which was 23 Gauge (outer diameter: 0.65 mm, and internal diameter: 0.40 mm) and which had a length of 30 mm, a large diameter part 30 which was 13 Gauge (outer diameter: 1.20 mm, and internal diameter: 0.94 mm), and a tapered part (unillustrated) which caused the front-end small diameter part 10 to be in communication with the large diameter part 30, had a length that was 7 mm and had an average gradient that was 6%. The length from the tip of the front-end small diameter part 10 to the basal end of the large diameter part 30 was 300.

The necessary times for aspirating 1 ml at an aspiration pressure of 100 mmHg were 21.6 seconds, 22.8 seconds, and 23.6 seconds. In addition, the necessary times for aspirating 1 ml at an aspiration pressure of 200 mmHg were 13.0 seconds, 13.4 seconds, and 12.9 seconds.

As explained above, according to this embodiment, oocytes are collectable from not only a dominant follicle bat also small follicles through the sequential oocyte collection procedure. In particular, the front-end small diameter part 10 has an outer diameter that is equal to or smaller than 0.7 mm, and has an inclination angle of the front end that is 10-20 degrees. This enables the puncturing of small follicles which contain oocytes that can be matured by subsequent in-vitro maturation. In addition, in view of the size of the cumulus oocyte complex and the allowable deformation level thereof, the front-end small diameter part is formed so as to have an internal diameter that is equal to or greater than 0.35 mm and have a length that is substantially the same as or slightly longer than the size of the dominant follicle based on the size of the dominant follicle, and the intermediate part is formed so as to have an internal diameter that is equal to or greater than 0.45 mm which is substantially the same size as that of the cumulus oocyte complex. This reduces the necessary aspiration time, and even if the cumulus oocyte complex is deformed at the time of aspiration by the front-end small diameter part, the deformed cumulus oocyte complex can be recovered speedily. Hence, the adverse effect on the oocyte when the entire cumulus oocyte complex is aspirated is reduced, enabling safer and securer oocyte collection. In addition, only the front-end small diameter part is inserted in both the dominant follicle and the small follicle, thus facilitating the oocyte collection procedure.

Still further, by forming the intermediate part that has an outer diameter equal to or smaller than 0.9 mm, and a first tapered part which is provided between the front-end small diameter part and the intermediate part, and which has an average gradient of substantially 6%, pain when the needle is inserted in human tissue is eased, enabling oocyte collection without anesthesia.

Yet still further, by collecting oocytes using this oocyte collection needle from the dominant follicle and from the small follicles in the natural cycle, multiple oocytes are collectable even in the case of the natural cycle, making an oocyte collection using hormonal agents unnecessary. Hence, adverse effects of the human body are available.

REFERENCE SIGNS LIST

1 Oocyte collection needle
10 Front-end small diameter part
12 First tapered part
15 Inclined acicular end
16 Inclined end surface
20 Intermediate part
23 Second diameter part
30 Large diameter part
50 Oocyte
51 Cumulus oocyte complex
60 Dominant follicle
61 Small follicle
70 Ovary

The invention claimed is:

1. An oocyte collection needle comprising:
   a small diameter part and a large diameter part which is fluidly in communication with the small diameter part, the small diameter part having a length that will not allow the large diameter part to penetrate a tissue of a human body,
   the small diameter part comprising a front-end small diameter part and an intermediate part,
   the front-end small diameter part being provided with a front end to be inserted in a human body,
   the intermediate part being in communication with the front-end small diameter part via a first tapered part fluidly in communication with the front-end small diameter part, the intermediate part having a larger internal diameter and outer diameter than an internal diameter and outer diameter of the front-end small diameter part, respectively; and
   the large diameter part being in communication with the intermediate part via a second tapered part fluidly in communication with the intermediate part, the large diameter part having a larger internal diameter and outer diameter than the internal diameter and the outer diameter of the intermediate part, respectively,
   wherein:
   the internal diameter of the front-end small diameter part is made so as to be equal to or greater than approximately 0.35 mm, the outer diameter of the front-end small diameter part is made so as to be equal to or smaller than approximately 0.7 mm, and a length of the front-end small diameter part is approximately 10-30 mm;
   the front end of the front-end small diameter part is formed as an inclined end having an inclination angle of approximately 10-20 degrees; and
   the internal diameter of the intermediate part is made so as to be equal to or greater than approximately 0.45 mm, the outer diameter of the intermediate part is equal to or smaller than approximately 0.9 mm; and
   a length, including the front-end small diameter part, the first tapered part, and the intermediate part, is approximately 60-130 mm.

2. The oocyte collection needle according to claim 1, wherein an average gradient of an internal diameter of the first tapered part is equal to or smaller than approximately 10%.

3. The oocyte collection needle according to claim 2, wherein a total length, including the front-end small diameter part, the first tapered part, the intermediate part, the second tapered part, and the large diameter part, is approximately 200-500 mm.

4. The oocyte collection needle according to claim 2, wherein the average gradient of the first tapered part is approximately 6%.

5. The oocyte collection needle according to claim 1, wherein the inclination angle of the front end of the front-end small diameter part is approximately 12-17 degrees.

6. The oocyte collection needle according to claim 1, wherein the internal diameter of the front-end small diameter part is approximately 0.35 mm, and the internal diameter of the intermediate part is approximately 0.45 mm.

* * * * *